(12) United States Patent
Aloni et al.

(10) Patent No.: US 7,553,665 B2
(45) Date of Patent: Jun. 30, 2009

(54) PROCESS FOR THE CULTIVATION OF MAMMALIAN CELLS PRODUCING IL-18BP IN SERUM-FREE CELL CULTURE MEDIUM

(75) Inventors: Yehoshua Aloni, Zur Yigal (IL); Orit Aharonovitz, Mazkeret Batya (IL); Thierry Ziegler, Leognan (FR)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 10/590,212

(22) PCT Filed: Feb. 28, 2005

(86) PCT No.: PCT/EP2005/050855

§ 371 (c)(1),
(2), (4) Date: Aug. 21, 2006

(87) PCT Pub. No.: WO2005/083058

PCT Pub. Date: Sep. 9, 2005

(65) Prior Publication Data

US 2007/0196895 A1 Aug. 23, 2007

Related U.S. Application Data

(60) Provisional application No. 60/551,171, filed on Mar. 8, 2004.

(30) Foreign Application Priority Data

Mar. 1, 2004 (EP) .................. 04100800

(51) Int. Cl.
*C12N 5/00* (2006.01)
*C12N 5/02* (2006.01)
*C07K 14/00* (2006.01)
*C07K 17/00* (2006.01)

(52) U.S. Cl. .................. 435/390; 530/350; 435/384

(58) Field of Classification Search .................. None
See application file for complete search history.

(56) References Cited

U.S. PATENT DOCUMENTS

| | | | |
|---|---|---|---|
| 6,406,909 B1 * | 6/2002 | Shibuya et al. | 435/404 |
| 2007/0037734 A1 | 2/2007 | Rossi et al. | |
| 2007/0134761 A1 | 6/2007 | Chatellard et al. | |
| 2007/0258962 A1 | 11/2007 | Chatellard et al. | |
| 2007/0293658 A1 | 12/2007 | Kornmann et al. | |
| 2008/0076708 A1 | 3/2008 | Altarocca et al. | |

FOREIGN PATENT DOCUMENTS

| WO | WO 96/26266 A1 | 8/1996 |
|---|---|---|
| WO | WO 98/15614 A1 | 4/1998 |
| WO | WO 99/09063 * | 2/1999 |
| WO | WO 01/18175 A1 | 3/2001 |
| WO | WO 01/23527 A1 | 4/2001 |
| WO | WO 02/077202 A1 | 10/2002 |
| WO | WO 2004/005493 A1 | 1/2004 |
| WO | WO 2004/081167 A2 | 9/2004 |
| WO | WO 2004/101617 A1 | 11/2004 |
| WO | WO 2005/040384 A1 | 5/2005 |
| WO | WO 2005/049649 A1 | 6/2005 |
| WO | WO 2006/003134 A1 | 1/2006 |
| WO | WO 2006/128908 A1 | 12/2006 |
| WO | WO 2006/131550 A1 | 12/2006 |

OTHER PUBLICATIONS

Altschul, S. F. et al. "Basic Local Alignment Search Tool", *J. Mol. Biol.*, 1990, pp. 403-410, vol. 215.
Altschul, S. F. et al. "Gapped Blast and PSI-Blast: A New Generation of Protein Database Search Programs", *Nucleic Acids Research*, 1997, 3389-3402, vol. 25, No. 17.
Bohak, Z. et al. "Novel Anchorage Matrices for Suspension Culture of Mammalian Cells", *Biopolymers*, 1987, pp. S205-S213, vol. 26.
Devereux, J. et al. "A Comprehensive Set of Sequence Analysis Programs for the VAX", *Nucleic Acids Research*, 1984, pp. 387-395, vol. 12, No. 1.
Grantham, R. "Amino Acid Difference Formula to Help Explain Protein Evolution", *Science*, Sep. 6. 1974, pp. 862-864, vol. 185, No. 4154.
Kim, S.-H. et al. "Structural Requirements of Six Naturally Occurring Isoforms of the IL-18 Binding Protein to Inhibit IL-18", *PNAS*, Feb. 1, 2000, pp. 1190-1195, vol. 97, No. 3.
Novick, D. et al. "Interleukin-18 Binding Protein: A Novel Modulator of the Th1 Cytokine Response", *Immunity*, Jan. 1999, pp. 127-136, vol. 10.
Pearson, W. R. "Rapid and Sensitive Sequence Comparison with FASTP and FASTA", *Methods in Enzymology*, pp. 63-98, vol. 183, No. 5.
Petti, S. A. et al. "Three-Dimensional Mammalian Cell Growth on Nonwoven Polyester Fabric Disks", *Biotechnol. Prog.*, 1994, pp. 548-550, vol. 10, No. 5.
Puck, T. T. et al. "Genetics of Somatic Mammalian Cells. III. Long-Term Cultivation of Euploid Cells from Human and Animal Subjects", *The Journal of Experimental Medicine*, 1958, pp. 945-956 and plates 63 and 64, vol. 108.
"C5467 CHO Medium", Sigma Aldrich 2003 Catalog, 2003, p. 423, XP002284128.
Focus on Alternatives: "Serum-Free Media for Cell Culture", Focus on Alternatives, 'Online!, Aug. 2003, pp. 1-30, XP002284129.
Wong, T. "Customization of Cell Culture Media for Optimal CHO Applications", Invitrogen Internet Catalog, 'Online!, Jul. 24, 2003, pp. 1-47, XP002284130.
Liu, C.-H. et al. "Factorial Designs Combined with the Steepest Ascent Method to Optimize Serum-Free Media for CHO Cells", *Enzyme and Microbial Technology*, Mar. 8, 2001, pp. 314-321, vol. 28, No. 4-5, XP001181835.
Pending claims in U.S. Appl. No. 11/916,087, filed Nov. 30, 2007, not yet published.
Pending claims in U.S. Appl. No. 11/915,453, filed Nov. 26, 2007, not yet published.

* cited by examiner

*Primary Examiner*—Robert Landsman
*Assistant Examiner*—Ian Dang
(74) *Attorney, Agent, or Firm*—Saliwanchik, Lloyd & Saliwanchik

(57) ABSTRACT

The invention relates to a process for culturing IL-18BP expressing mammalian cells under serum-free conditions.

17 Claims, 2 Drawing Sheets

PROCESS FOR THE CULTIVATION OF MAMMALIAN CELLS PRODUCING IL-18BP IN SERUM-FREE CELL CULTURE MEDIUM

CROSS-REFERENCE TO RELATED APPLICATION

This application is the U.S. national stage application of International Patent Application No. PCT/EP2005/050855, filed Feb. 28, 2005, which claims the benefit of U.S. Provisional Patent Application No. 60/551,171, filed Mar. 8, 2004, the disclosures of which are hereby incorporated by reference in their entireties, including all figures, tables and amino acid or nucleic acid sequences.

FIELD OF THE INVENTION

The present invention is in the field of cultivation of mammalian cells under serum-free culture conditions In particular, it relates to the growth of mammalian cells such as Chinese hamster ovary (CHO) cells. The cells produce a recombinant protein called interleukin-18 binding protein (IL-18BP).

BACKGROUND OF THE INVENTION

The present invention relates to a process using a serum-free medium for the growth and maintenance of mammalian cells in culture.

Cell culture is widely used today for the production of various biologically active products, such as viral vaccines, monoclonal antibodies, non-antibody immuno-regulators, polypeptide growth factors, hormones, enzymes, tumor specific antigens, etc. These products are produced by normal or transformed and genetically engineered cells.

For culturing cells, in the past the culture medium was supplemented with serum, which serves as a universal nutrient for the growth and maintenance of all mammalian cell lines that produce biologically active products. Serum contains hormones, growth factors, carrier proteins, attachment and spreading factors, nutrients, trace elements, etc. Culture media usually contained up to about 10% of animal serum, such as fetal bovine serum (FBS), also called fetal calf serum (FCS).

Although widely used, serum has many limitations. It contains high levels of numerous proteins interfering with the limited quantities of the desired protein of interest produced by the cells. These proteins derived from the serum must be separated from the product during downstream processing such as purification of the protein of interest, which complicates the process and increases the cost.

The advent of BSE (Bovine Spongiform Encephalopathy), a transmissible neurodegenerative disease of cattle with a long latency or incubation period, has raised regulatory concerns about using animal-derived sera in the production of biologically active products.

There is therefore a great demand for the development of alternative media free from animal sources that support cell growth and maintain cells during the production of biologically active products.

Generally, cell culture media comprise many components of different categories, such as amino acids, vitamins, salts, fatty acids, and further compounds:

Amino acids: For instance, U.S. Pat. No. 6,048,728 (Inlow et al.) discloses that the following amino acids may be used in a cell culture medium: Alanine, Arginine, Aspartic Acid, Cysteine, Glutamic Acid, Glutamin, Glycine, Histidine, Isoleucine, Leucine, Lysine, Methionine, Phenyalanine, Proline, Serine, Tryptophan, Tyrosine, Threonine, and Valine.

Vitamins: US 2003/0096414 (Ciccarone et al.) or U.S. Pat. No. 5,811,299 (Renner et al.) for example describe that the following vitamins may be used in a cell culture medium: Biotin, Pantothenate, Choline Chloride, Folic Acid, Myo-Inositol, Niacinamide, Pyridoxine, Riboflavin, Vitamin B12, Thiamine, Putrescine.

Salts: For instance, U.S. Pat. No. 6,399,381 (Blum et al.) discloses a medium comprising $CaCl_2$, KCl, $MgCl_2$, NaCl, Sodium Phosphate Monobasic, Sodium Phosphate Dibasic, Sodium Selenite, $CuSO_4$, $ZnCl_2$. Another example for a document disclosing the inorganic salts that may be used in a culture medium is US 2003/0153042 (Arnold et al.), describing a medium comprising $CaCl_2$, KCl, $MgCl_2$, NaCl, Sodium Phosphate Monobasic, Sodium Phosphate Dibasic, $CuCl_2 \cdot 2H_2O$, $ZnCl_2$.

Fatty acids: Fatty acids that are known to be used in media are Arachidonic Acid, Linoleic Acid, Oleic Acid, Lauric Acid, Myristic Acid, as well as Methyl-beta-Cyclodextrin, see e.g. U.S. Pat. No. 5,045,468 (Darfler). It should be noted that cyclodextrin is not a lipid per se, but has the ability to form a complex with lipids and is thus used to solubilize lipids in the cell culture medium.

Further components, in particular used in the frame of serum-free cell culture media, are compounds such as glucose, glutamine, Na-pyruvate, insulin or ethanolamine (e.g. EP 274 445), or a protective agent such as Pluronic F68. Pluronic® F68 (also known as Poloxamer 188) is a block copolymer of ethylene oxide (EO) and propylene oxide (PO).

Standard "basic media" are also known to the person skilled in the art. These media already contain several of the medium components mentioned above. Examples of such media that are widely applied are Dulbecco's Modified Eagle's Medium (DMEM), Roswell Park Memorial Institute Medium (RPMI), or Ham's medium.

For the development and supply of biologically active products, such as therapeutic proteins or vaccines, large amounts must be produced. Suitable cells that are widely used for production of polypeptides turned out to be Chinese Hamster Ovary (CHO) cells.

CHO cells were first cultured by Puck (J. Exp. Med. 108, 945, 1958) from a biopsy of an ovary from a female Chinese hamster. From these original cells a number of sub-lines were prepared with various characteristics. One of these CHO cell lines, CHO-K1, is proline-requiring and is diploid for the dihydrofolate reductase (DHFR) gene. Another line derived from this cell line is a DHFR deficient CHO cell line (CHO DUK B11) (PNAS 77, 1980, 4216-4220), which is characterized by the loss of DHFR function as a consequence of a mutation in one DHFR gene and the subsequent loss of the other gene.

Further cells that are frequently used for the production of proteins intended for administration to humans are human cell lines such as the human fibrosarcoma cell line HT1080 or the human embryonic kidney cell line 293.

One therapeutic protein of interest is Interleukin-18 binding protein (IL-18BP). IL-18BP is a soluble protein having a high affinity for IL-18. It was first isolated from human urine, and the human and mouse cDNAs as well as the human gene were cloned (Novick et al., 1999; WO 99/09063). The protein has been designated IL-18 binding protein (IL-18BP). The International non-proprietary name of IL-18BP is tadekinig alpha.

IL-18BP is not the extracellular domain of one of the known IL-18 receptors, but a secreted, naturally circulating protein. It belongs to a novel family of secreted proteins, further including several Poxvirus-encoded proteins (Novick et al., 1999). Urinary as well as recombinant IL-18BP specifically bind IL-18 with a high affinity and modulate the biological affinity of IL-18.

The IL-18BP gene was localized to the human chromosome 11q13, and no exon coding for a transmembrane domain was found in an 8.3 kb genomic sequence. Four splice variants or isoforms of IL-18BP generated by alternative mRNA splicing have been found in humans so far. They were designated IL-18BP a, b, c and d, all sharing the same N-terminus and differing in the C-terminus (Novick et al, 1999). These isoforms vary in their ability to bind IL-18. Of the four, IL-18BP isoforms a and c are known to have a neutralizing capacity for IL-18. Human IL-18BP isoform binds to murine IL-18.

IL-18BP has been suggested as a therapeutic protein in a number of diseases and disorders, such as psoriasis, Crohn's Disease, rheumatoid arthritis, psoriatic arthritis, liver injury, sepsis, atherosclerosis, ischemic heart diseases, allergies, etc., e.g. disclosed in WO9909063, WO0107480, WO0162285, WO0185201, WO02060479, WO02096456, WO03080104, WO02092008, WO02101049, WO03013577.

There is thus a need for an efficient manufacturing process for the production of IL-18BP in cell culture, and preferably a process that is operated under serum-free conditions.

SUMMARY OF THE INVENTION

The present invention is based on the development of a process for the cultivation of cells in a cell culture medium that is free from animal serum-derived components and at the same time highly effective for cell growth and maintenance of mammalian cell culture. Cultivation of the cells is carried out for the production of proteins in the cells.

In accordance with the present invention, the cells produce IL-18BP or have been modified to produce IL-18BP. The protein can be isolated and purified from the cell culture medium (supernatant) and formulated into a pharmaceutical composition destined for administration into humans or animals.

Therefore, in a first aspect, the invention relates to a process for the cultivation of cells producing IL-18BP, comprising the step of growing the cells in a cell culture medium free of components derived from animal serum, wherein the cell culture medium comprises:

Asparagine at a concentration ranging from about 800 to about 900 mg/L;
Natrium Chloride at a concentration ranging from about 3000 to about 4500 mg/L;
Selenite at a concentration ranging from about 0.005 to about 0.015 mg/L;
Wheat hydrolysate at a concentration ranging from about 5000 to about 15000 mg/L; and
Insulin at a concentration ranging from about 2.5 to about 6 mg/L.

In a second aspect, the invention relates to a process for the production of IL-18BP comprising the step of cultivating cells expressing IL-18BP in a cell culture medium free of components derived from animal serum, wherein the cell culture medium comprises:

Asparagine at a concentration ranging from about 800 to about 900 mg/L;
Natrium Chloride at a concentration ranging from about 3000 to about 4500 mg/L;
Selenite at a concentration ranging from about 0.005 to about 0.015 mg/L;
Wheat hydrolysate at a concentration ranging from about 5000 to about 15000 mg/L; and
Insulin at a concentration ranging from about 2.5 to about 6 mg/L.

A third aspect of the invention relates to the use of a medium according to the invention for the production of a protein of interest.

In a fourth aspect, the invention relates to the use of the medium of the invention for growth of cells in culture.

A fifth aspect of the invention relates to the use of a medium according to the invention for the maintenance of cells in culture during production phase of a polypeptide of interest.

BRIEF DESCRIPTION OF THE DRAWINGS

FIG. 1 shows the viable cell density;

DETAILED DESCRIPTION OF THE INVENTION

Figure 1:
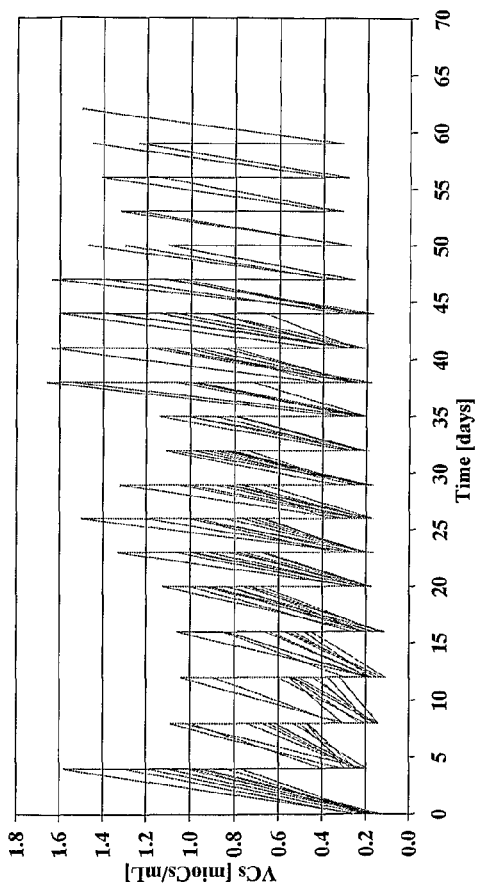
FIG. 1 IL-18BP expressing CHO cells were cultured in suspension in serum-free medium according to the invention with repeated dilutions with fresh medium for 60 days (n=10).
Figure 2:
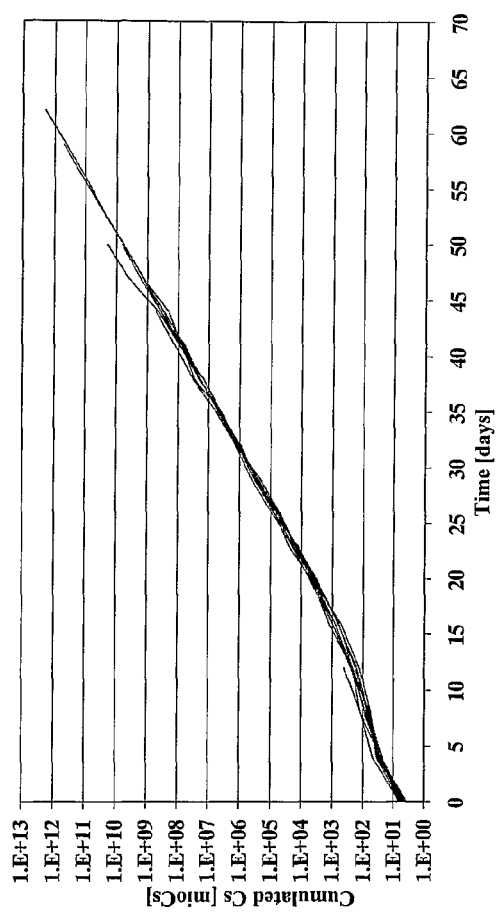
FIG. 2 shows the cumulated viable cells.
Figure 3:
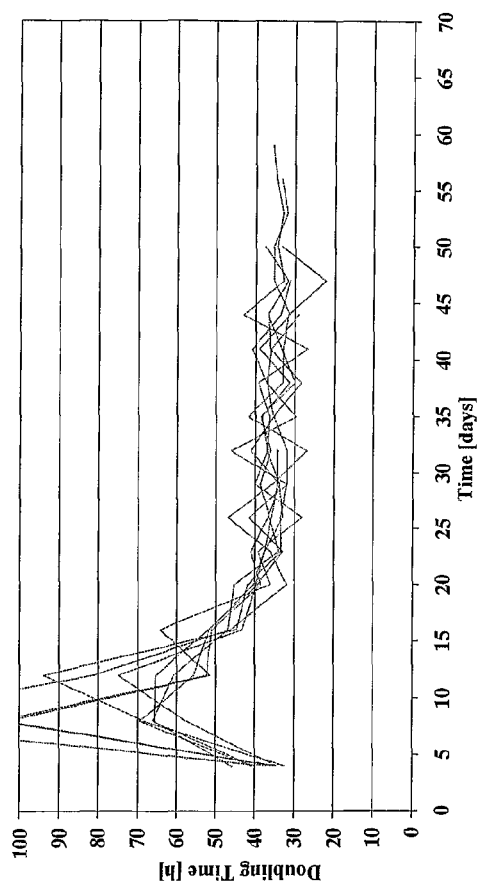
FIG. 3 shows the doubling time.
Figure 4:
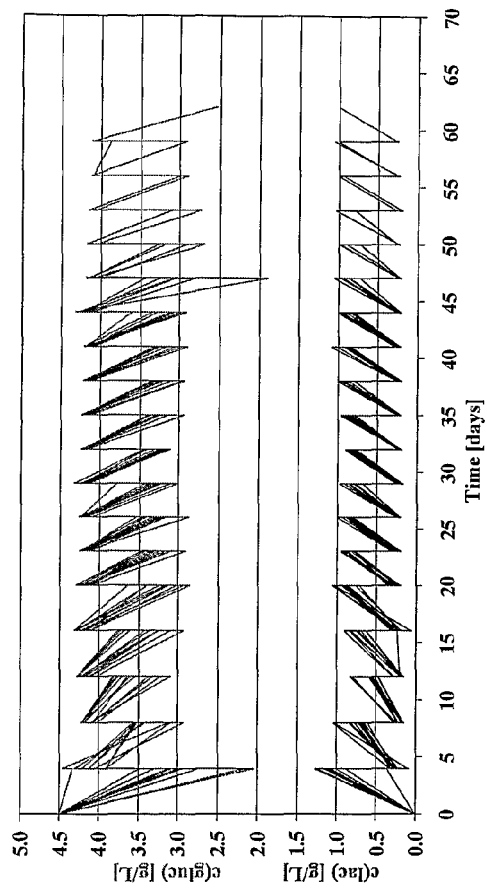
FIG. 4 shows the glucose and lactate concentration in the supernatant.

The present invention is based on the development of a process for the growth and maintenance of IL-18BP expressing cells, and for the production of IL-18BP, in a cell culture medium that is free from serum-derived components.

Therefore, the present invention relates to a process for the production of IL-18BP, comprising the step of cultivating a cell expressing IL-18BP in a cell culture medium free of components derived from animal serum, wherein the cell culture medium comprises:

Asparagine at a concentration ranging from about 700 to about 1000 mg/L, preferably from about 800 to about 900 mg/L;
Natrium Chloride at a concentration ranging from about 2000 to about 5000, preferably from about 3000 to about 4500 mg/L;
Selenite at a concentration ranging from about 0.003 to about 0.02 mg/L, preferably from about 0.005 to about 0.015 mg/L;
Wheat hydrolysate at a concentration ranging from about 3000 to about 20000 mg/L, preferably from about 5000 to about 15000 mg/L; and
Insulin at a concentration ranging from about 1 to about 8 mg/L, preferably from about 2.5 to about 6 mg/L.

The invention further relates to a process of cultivating an IL-18BP expressing cells, comprising the step of growing the cell in a cell culture medium free of components derived from animal serum, wherein the cell culture medium comprises:

Asparagine at a concentration ranging from about 700 to about 1000 mg/L, preferably from about 800 to about 900 mg/L;
Natrium Chloride at a concentration ranging from about 2000 to about 5000, preferably from about 3000 to about 4500 mg/L;
Selenite at a concentration ranging from about 0.003 to about 0.02 mg/L, preferably from about 0.005 to about 0.015 mg/L;
Wheat hydrolysate at a concentration ranging from about 3000 to about 20000 mg/L, preferably from about 5000 to about 15000 mg/L; and Insulin at a concentration ranging from about 1 to about 8 mg/L, preferably from about 2.5 to about 6 mg/L.

Preferably, the process further comprises the step of collecting the medium comprising the protein of interest.

In a further preferred embodiment, the process further comprises isolating the protein of interest.

In a further preferred embodiment, the process further comprises formulating the isolated protein with a pharmaceutically acceptable carrier to obtain a pharmaceutical composition.

In a third aspect, the invention relates to the use cell culture medium comprising
- Asparagine at a concentration ranging from about 700 to about 1000 mg/L, preferably from about 800 to about 900 mg/L;
- Natrium Chloride at a concentration ranging from about 2000 to about 5000, preferably from about 3000 to about 4500 mg/L;
- Selenite at a concentration ranging from about 0.003 to about 0.02 mg/L, preferably from about 0.005 to about 0.015 mg/L;
- Wheat hydrolysate at a concentration ranging from about 3000 to about 20000 mg/L, preferably from about 5000 to about 15000 mg/L; and
- Insulin at a concentration ranging from about 1 to about 8 mg/L, preferably from about 2.5 to about 6 mg/L for the production of a polypeptide of interest.

In a fourth aspect, the invention relates to the use of a cell culture medium comprising
- Asparagine at a concentration ranging from about 700 to about 1000 mg/L, preferably from about 800 to about 900 mg/L;
- Natrium Chloride at a concentration ranging from about 2000 to about 5000, preferably from about 3000 to about 4500 mg/L;
- Selenite at a concentration ranging from about 0.003 to about 0.02 mg/L, preferably from about 0.005 to about 0.015 mg/L;
- Wheat hydrolysate at a concentration ranging from about 3000 to about 20000 mg/L, preferably from about 5000 to about 15000 mg/L; and
- Insulin at a concentration ranging from about 1 to about 8 mg/L, preferably from about 2.5 to about 6 mg/L for the growth of cells expressing IL-18BP in in culture.

In a fifth aspect, the invention relates to the use of a cell culture medium comprising
- Asparagine at a concentration ranging from about 700 to about 1000 mg/L, preferably from about 800 to about 900 mg/L;
- Natrium Chloride at a concentration ranging from about 2000 to about 5000, preferably from about 3000 to about 4500 mg/L;
- Selenite at a concentration ranging from about 0.003 to about 0.02 mg/L, preferably from about 0.005 to about 0.015 mg/L;
- Wheat hydrolysate at a concentration ranging from about 3000 to about 20000 mg/L, preferably from about 5000 to about 15000 mg/L; and
- Insulin at a concentration ranging from about 1 to about 8 mg/L, preferably from about 2.5 to about 6 mg/L for the maintenance of cells expressing IL-18BP in culture, e.g. during production phase of a polypeptide of interest.

In accordance with the processes and uses of the present invention, the cell culture medium comprises:
- Asparagine at a concentration ranging from about 700 to about 1000 mg/L, preferably from about 800 to about 900 mg/L;
- Natrium Chloride at a concentration ranging from about 2000 to about 5000, preferably from about 3000 to about 4500 mg/L;
- Selenite at a concentration ranging from about 0.003 to about 0.02 mg/L, preferably from about 0.005 to about 0.015 mg/L;
- Wheat hydrolysate at a concentration ranging from about 3000 to about 20000 mg/L, preferably from about 5000 to about 15000 mg/L; and
- Insulin at a concentration ranging from about 1 to about 8 mg/L, preferably from about 2.5 to about 6 mg/L.

In the frame of the present invention, Asparagine may be used in any concentration ranging from about 700 to 1000 mg/L, e.g. at 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 675, 980, 985, 990, 995 mg/L.

In the frame of the present invention, Natrium Chloride may be used at a concentration ranging from about 2000 to about 5000 mg/L, e.g. at 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 mg/L.

In the frame of the present invention, Selenite may be used at a concentration ranging from about 0.003 to about 0.02 mg/L, e.g. at 0.0035, 0.004. 0.0045, 0.005, 0.0055, 0.006, 0.0065, 0.007, 0.0075, 0.008, 0.0085, 0.009, 0.0095, 0.01, 0.011, 0.012, 0.013, 0.014, 0.015, 0.016, 0.017, 0.018, 0.019, 0.02 mg/L.

In the frame of the present invention, Wheat hydrolysate may be used at a concentration ranging from about 3000 to about 20000 mg/L, e.g. at 3500, 4000, 4500, 5000, 5500, 6000, 6500, 7000, 7500; 8000, 8500, 9000, 9500, 9600, 9700, 9800, 9900, 10000, 10100, 10200, 10300, 10400, 10500, 10600, 10700, 10800, 10900, 11000, 11500, 12000, 12500, 13000, 13500, 14000, 14500, 15000, 15500, 16000, 16500, 17000, 18000, 18500, 19000, 19500 mg/L.

In the frame of the present invention, Insulin may be used at a concentration ranging from about 1 to about 8 mg/L, e.g. at 1.25, 1.5, 1.75, 2, 2.25, 2.5, 2.75, 3, 3.25, 3.5, 3.75, 4, 4.25, 4.5, 4.75, 5, 5.25, 5.5, 5.75. 6, 6.25, 6.5, 6.75, 7, 7.25, 7.5, 7.75, 8, 8.25, 8.5, 8.75 mg/L.

As shown in the Examples below, in the process of the invention using a medium comprising these components within the ranges indicated supported excellent cell growth and maintenance over an extended period of time.

The culturing step of the process of the invention may be carried out in any suitable environment, such as Petri dishes, T-flasks or roller bottles, but preferably in vessels having greater volumes such as e.g. a bioreactor. T-flasks and roller bottles are particularly suitable for the growth of cells, and for protein production the cells are preferably maintained in a bioreactor.

The cells to be used in the frame of the various aspects of the present invention are preferably mammalian cells. They may be of human or animal origin. Examples of mammalian cells that can be cultivated in the process according to the present invention include, e.g., 3T3 cells, COS cells, human osteosarcoma cells, MRC-5 cells, BHK cells, VERO cells, CHO cells, rCHO-tPA cells, rCHO—Hep B Surface Antigen cells, HEK 293 cells, rHEK 293 cells, rC127—Hep B Surface Antigen cells, Normal Human fibroblast cells, Stroma cells, Hepatocytes cells, PER.C6 cells and human permanent amniocytic cells. Examples of hybridomas that may be cultivated in the process according to the present invention include, e.g., DA4.4 cells, 123A cells, 127A cells, GAMMA cells and 67-9-B cells.

It is highly preferred to cultivate a Chinese Hamster Ovary cell (CHO cell) in accordance with the present invention.

The cells cultured in accordance with the present invention may grow in suspension or, for anchorage dependent cells, attached to a solid support. Microcarriers and Fibra-Cel® disks may be used in mammalian cell culture for the growth of anchorage-dependent cells and are among the established technological platforms for industrial production of proteins (see, e.g., Bohak et al. 1987; Petti et al. 1994).

In the frame of the processes and uses of the present invention, Asparagine is advantageously comprised as Asparagine.H$_2$O (TLC 99%, TLC being Thin Layer Chromatography).

Selenite may e.g. be comprised in the medium as sodium selenite.

Wheat hydrolysate is a plant-derived component, which is part of the medium of the invention based on the fact that cells can also use amino acids that are in peptide form. Peptides can range in size from two amino acids to many amino acids. Peptides that are derived by the hydrolysis of proteins provide a supplemental (undefined) source of amino acids in a form that supports superior growth of a number of cell lines/types.

The insulin to be used in the frame of the medium of the invention may be derived from any source and species, as long as it supports growth and maintenance of the particular cell line or cell type for which the medium is used. Preferably, insulin may be recombinant. It is further preferred that the insulin is derived from the species corresponding to species from which the cell line or cell type is derived, or that it is human insulin.

Preferred concentration ranges of the compounds of the medium to be used in the process of the invention are as follows:

Asparagine at a concentration ranging from about 810 to about 850 mg/L, most preferably about 830.

Natrium Chloride at a concentration ranging from about 3400 to about 3600 mg/L, most preferably about 3500 mg/L.

Selenite at a concentration ranging from about 0.01 to about 0.012 mg/L, most preferably about 0.0110 mg/L.

Wheat hydrolysate at a concentration ranging from about 8000 to about 12000 mg/L, most preferably about 10000 mg/L.

Insulin at a concentration ranging from about 3 to about 5 mg/L, most preferably about 4 mg/L.

In a preferred embodiment, the medium further comprises glucose at a concentration ranging from about 500 to about 5500 mg/L, preferably about 1000 mg/L or about 4500 or about 5000 mg/L In a further preferred embodiment, the medium comprises one or more amino acids. The amino acids are selected from Alanine, Arginine, Aspartic Acid, Cysteine, Glutamic Acid, Glycine, Histidine, Isoleucine, Leucine, Lysine, Methionine, Phenylalanine, Proline, Serine, Tryptophan, Tyrosine, Threonine, and Valine, but no Glutamine.

In an alternative embodiment, Glutamine is added to the medium. Glutamine may preferably be added to the medium during cell culture (e.g. growth, maintenance, production mode).

Preferably, the medium according to the invention further comprises vitamins. Vitamins that are preferred in the medium of the invention are selected from Biotin, Pantothenate, Choline chloride, Folic Acid, Myo-Inositol, Niacinamide, Pyridoxine, Riboflavin, Vitamin B12, Thiamine, and Putrescine.

The medium according to the invention preferably further comprises inorganic salts and trace elements. The ions are preferably Ca$^{2+}$, K$^+$, MG$^{2+}$, Na$^+$, Cl$^-$, Phosphate, Cu$^{2+}$, Zn$^{2+}$. Those salts and trace elements are preferably selected from CaCl$_2$ anhydrous, KCl, MgCl$_2$ anhydrous, NaCl, Sodium Phosphate Monobasic, Sodium Phosphate Dibasic, CuCl$_2$.2H$_2$0, and ZnCl$_2$.

Preferably, the medium of the invention further comprises a buffer. Many buffers may be used in the frame of the medium of the invention, such as sodium bicarbonate buffer, Tris, BES (N,N-Bis(2-hydroxyethyl)-2-aminoethanesulfonic acid), Glycine buffer, or the like. A zwitter ionic buffer is particularly useful for the medium of the invention. A preferred zwitter ionic buffer that may be used is HEPES (N-(2-Hydroxyethyl)piperazine-N'-2-ethanesulfonic acid) in acid form.

In yet another preferred embodiment, the medium further comprises fatty acids. Such fatty acids are preferably selected from Arachidonic Acid, Linoleic Acid, Oleic Acid, Lauric Acid, Myristic Acid, and Cyclodextrin, which is not a lipid per se but merely serves at solubilization of lipids in the medium. Cyclodextrin is preferably Methyl-beta-cyclodextrin.

Further hydrolysates may be used in the frame of the present invention, as long as they are not derived from animal sources. Preferably, the medium of the invention may further comprise a soy hydrolysate.

It is also preferred that the medium of the invention further comprises steroids such as e.g. cortisone or hydrocortisone, and/or further energy sources such as e.g. pyruvate, e.g. Na-pyruvate, and/or a protective agent such as Pluronic F68.

In the frame of the processes and uses of the present invention, any suitable known basic serum-free medium may be used, as long as the following compounds are present:

Asparagine at a concentration ranging from about 700 to about 1000 mg/L, preferably from about 800 to about 900 mg/L;

Natrium Chloride at a concentration ranging from about 2000 to about 5000, preferably from about 3000 to about 4500 mg/L;

Selenite at a concentration ranging from about 0.003 to about 0.02 mg/L, preferably from about 0.005 to about 0.015 mg/L;

Wheat hydrolysate at a concentration ranging from about 3000 to about 20000 mg/L, preferably from about 5000 to about 15000 mg/L; and Insulin at a concentration ranging from about 1 to about 8 mg/L, preferably from about 2.5 to about 6 mg/L.

Examples of known basic serum-free media are listed below:

| Medium | Manufacturer | Cat. No. |
| --- | --- | --- |
| EX-CELL 302 | JRH | 14312-1000M |
| EX-CELL 325 | JRH | 14335-1000M |
| CHO-CD3 | Sigma | C-1490 |
| CHO III PFM | Gibco | 96-0334SA |
| CHO-S-SFM II | Gibco | 12052-098 |
| CHO-DHFR | Sigma | C-8862 |
| ProCHO 5 | Cambrex | BE12-766Q |
| SFM4CHO | HyClone | SH30549.01 |
| Ultra CHO | Cambrex | 12-724Q |
| HyQ PF CHO | HyClone | SH30220.01 |

-continued

| Medium | Manufacturer | Cat. No. |
|---|---|---|
| HyQ SFX CHO | HyClone | SH30187.01 |
| HyQ CDM4CHO | HyClone | SH30558.01 |
| IS CHO-CD | Irvine Scientific | #91119 |
| IS CHO-V | Irvine Scientific | #9197 |

The processes and uses of the invention preferably serve to produce a polypeptide of interest.

The polypeptide of interest may be, e.g., a naturally secreted protein, a normally cytoplasmic protein, a normally transmembrane protein, or a human or a humanized antibody. When the protein of interest is a normally cytoplasmic or a normally transmembrane protein, the protein has preferably been engineered in order to become soluble.

The polypeptide of interest may be of any origin. Preferred polypeptides of interest are of human origin, and more preferably, the proteins of interest are therapeutic proteins.

The protein of interest may be a hormone, a cytokine-binding protein, an interferon, a soluble receptor, or an antibody.

Therapeutic proteins that may be produced according to a method of the present invention include, e.g., chorionic gonadotropin, follicle-stimulating hormone, lutropin-choriogonadotropic hormone, thyroid stimulating hormone, human growth hormone, interferons (e.g., interferon beta-1a, interferon beta-1b), interferon receptors (e.g., interferon gamma receptor), TNF receptors p55 and p75, TACl-Fc fusion proteins, interleukins (e.g., interleukin-2, interleukin-11), interleukin binding proteins (e.g., interleukin-18 binding protein), anti-CD11a antibodies, erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof.

The polypeptide may particularly be selected from the group consisting of chorionic gonadotropin (CG), follicle-stimulating hormone (FSH), lutropin-choriogonadotropic hormone (LH), thyroid stimulating hormone (TSH), human growth hormone (hGH), interferons (e.g., interferon beta-1a, interferon beta-1b), interferon receptors (e.g., interferon gamma receptor), TNF receptors p55 and p75, interleukins (e.g., interleukin-2, interleukin-11), interleukin binding proteins (e.g., interleukin-18 binding protein), anti-CD11a antibodies, and muteins, fragments, soluble forms, functional derivatives, fusion proteins thereof.

Further polypeptides of interest include, e.g., erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof.

Should the protein of interest be formulated with a pharmaceutically acceptable carrier, the result of the process is a pharmaceutical composition.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The pharmaceutical composition formulated according to the invention may then be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The processes and uses of the present invention aim at production of interleukin-18 binding protein (IL-18BP).

IL-18BP may be native, i.e. naturally occurring IL-18BP. Preferably, the IL-18BP to be produced is of human origin. Since IL-18BP is a soluble, secreted protein, it is released into the cell culture supernatant, either by means of its natural signal peptide, or by means of a heterologous signal peptide, i.e. a signal peptide derived from another secreted protein which may be more efficient in the particular expression system used.

The term "IL-18 binding protein" is used herein synonymously with "IL-18BP". This term relates to IL-18 binding proteins such as the ones defined in WO 99/09063 or in Novick et al., 1999. The term IL-18BP includes splice variants and/or isoforms of IL-18 binding proteins, as the ones defined in Kim et al., 2000, in particular human isoforms a and c of IL-18BP. The term "IL-18PB", as used herein, further includes muteins, functional derivatives, active fractions, fused proteins, circularly permutated proteins and slats of IL-18BP as defined in WO 99/09063.

The IL-18BP that is produced by using the medium of the present invention is preferably glycosylated.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-18BP or encodes a viral IL-18BP (WO 99/09063) under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nlh.gov) and FASTA (Pearson W R, 1990).

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mutein has at least 40% identity or homology with the sequence of either an IL-18BP or a virally-encoded IL-18BP homologue, as defined in WO 99/09063. More preferably, it has at least 50%, at least 60%, at least 70%, at least 80% or, most preferably, at least 90% or 95% identity or homology thereto.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

The sequences of IL-18BP and its splice variants/isoforms can be taken from WO99/09063 or from Novick et al., 1999, as well as from Kim et al., 2000.

Should the IL-18BP of the invention be used as a pharmaceutical composition, such pharmaceutical composition may be used for treatment and/or prevention of a number of diseases or disorders. Such diseases or disorders are preferably IL-18 mediated disorders. In particular, purified IL-18BP may be used for treatment and/or prevention of psoriasis, psoriatic arthritis, Crohn's Disease, rheumatoid arthritis, liver injury such as alcoholic liver cirrhosis, sepsis, atherosclerosis, ischemic heart diseases, allergies, in particular delayed-type hypersensitivity, and closed head injury, as disclosed in WO9909063, WO0107480, WO0162285, WO0185201, WO02060479, WO02096466, WO03080104, WO02092008, WO02101049, WO03013577.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLE 1

Growth of IL-18BP Expressing CHO Cells in Serum Free Medium 1.1. Preparation of Serum-Free Medium (SFM) Designated "SM-005"

The cell culture medium that was used for the experiments described under 1.2. was a medium adapted to contain the following components in the following concentrations:

Asparagine at a concentration of 830 mg/L;
Natrium Chloride at a concentration of 3500 mg/L;
Selenite at a concentration of 0.0110 mg/L;
Wheat hydrolysate at a concentration of 10000 mg/L; and
Insulin at a concentration of 4 mg/L.

This medium also contained 4.5 g/l of glucose. If the medium is used for production mode, the glucose concentration may be decreased to 1 g/l. The medium further contained all amino acids but for Glutamine. Vitamins, salts, fatty acids, HEPES as a buffer, Pluronic F68, Hydrocortisone, Na Pyruvate and Soy Hydrolysate were also present in this medium. The medium is identified below as SM-005.

1.2. Growth of Cells in Suspension

T-flasks or roller bottles were inoculated with cells from an IL-18BP expressing and secreting CHO clone that had previously been established. These cells grow in suspension and were first expanded. During the cell expansion process, cells were cultured in suspension and systematically diluted with defined volumes of fresh SM-005 medium at fixed days. For monitoring purposes, cell density, glucose- and lactate concentration were measured at each dilution step (see figures).

At day 0, a vial from the previously established Master Cell Bank was thawed. The cells originating from this vial were then inoculated into a 75 cm$^2$ Tissue Culturing Flask (TCF 75 cm$^2$) in a total volume of 30 mL of fresh SM-005 medium. The resulting cell concentration in the TCF reached approximately 0.20 million cells/mL. Finally, the TCF was incubated under agitation at a temperature of 37° C.

At day 4, the culture was transferred to a TCF175 cm$^2$ and diluted to 120 mL by adding fresh and preheated medium SM-005.

At day 8, the culture was transferred to a RB850 cm$^2$ and diluted to 400 mL by adding fresh and preheated medium SM-005.

At day 12, the culture was diluted to 1200 mL (dilution ratio of 1/3) by adding fresh and preheated medium SM-005 and then split into 3 roller bottles RB850 cm$^2$, each containing 400 mL.

At day 16, the culture was diluted to 4800 mL (dilution ratio of 1/4) by adding fresh and preheated medium and then split into 6 RB1750 cm2, each containing 800 mL.

From day 20 (D20, D23, D26, . . . up to D62), the RB1750 cm$^2$ were diluted in a repetitive manner every 3 days, respecting a dilution ratio of 1/4. At each dilution day, the required number of RB1750 cm$^2$ was generated (at least 4 RB1750 cm$^2$). Thus, each RB1750 cm$^2$ were diluted from 800 mL to 3200 mL by adding fresh and preheated medium and then split into 4 RB1750 cm$^2$, each containing 800 mL.

In order to inoculate bioreactors, the required number of roller bottles were harvested on a dilution day (between D20 and D60), pooled in a sterile glass-bottle, and transferred into bioreactors.

TABLE 1

Schematic description of the inoculum preparation process. From day 20 on, cells were diluted with a fixed dilution ratio of 1/4.

| Day | Operation | Volume |
| --- | --- | --- |
| 0 | Thawing<br>MCB Vial → 75 cm$^2$ TCF | 30 mL |
| 4 | Dilution with fresh medium<br>75 cm$^2$ TCF → 150 cm$^2$ TCF | 120 mL |
| 8 | Dilution with fresh medium<br>150 cm$^2$ TCF → 850 cm$^2$ RB | 400 mL |
| 12 | Dilution with fresh medium<br>1 × 850 cm$^2$ RB → 3 × 850 cm$^2$ RB | 1200 mL |
| 16 | Dilution with fresh medium<br>3 × 850 cm$^2$ RB → 6 × 1750 cm$^2$ RB | 4800 mL |
| From D20 on, every 3 days | Dilution with fresh medium<br>Repetitive dilutions with a 1/4 split ratio in RB1750 cm$^2$. | 800 mL per RB1750 cm$^2$ |
| Dilution day<br>D20 ≦ D ≦ D62 | Harvesting of the cell inoculum for bioreactor seeding. | |

FIGS. 1 to 4 show the data measured during the inoculum preparation process (n=10). FIG. 1 shows the viable cell density, FIG. 2 the cumulated viable cells, FIG. 3 the doubling time, and FIG. 4 the glucose and lactate concentration in the supernatant.

After a 20-day adaptation phase, growth of the cells is very consistent and reproducible in the serum-free medium. The stable growth conditions enable to subculture cells easily by repeated dilution with a ratio 1:4 over extended period of time (tested up to day 62, as shown in FIGS. 1,2,3,4).

REFERENCES

1. Altschul S F et al, J Mol Biol, 215, 403-410, 1990.
2. Ausubel et al., Current Protocols in Molecular Biology, supra, Interscience, N.Y., §§6.3 and 6.4 (1987, 1992).
3. Altschul S F et al, Nucleic Acids Res., 25:389-3402, 1997.

4. Bohak et al. 1987 Bohak Z, Kadouri A et al. (1987) "Novel anchorage matrices for suspension culture of mammalian cells" Biopolymers. 26 Suppl:S205-213.
5. Devereux J et al, Nucleic Acids Res, 12, 387-395, 1984.
6. Grantham et al., Science, Vol. 185, pp. 862-864 (1974).
7. Kim S H, Eisenstein M, Reznikov L, Fantuzzi G, Novick D, Rubinstein M, Dinarello C A. Structural requirements of six naturally occurring isoforms of the IL-18 binding protein to inhibit IL-18. Proc Natl Acad Sci USA 2000; 97:1190-1195.
8. Novick, D, Kim, S-H, Fantuzzi, G, Reznikov, L, Dinarello, C, and Rubinstein, M (1999). Immunity 10, 127-136.
9. Pearson, Methods Enzymol. 1990; 183:63-98.
10. Petti S A, Lages A C et al. (1994) "Three-dimensional mammalian cell growth on nonwoven polyester fabric disks" Biotechnol Prog. 10(5):548-550.
11. Puck et al., J. Exp. Med. 108, 945, 1958

The invention claimed is:

1. A process for the cultivation of cells producing interleukin-18 binding protein (IL-18BP) or the production of IL-18BP comprising cultivating a cell expressing IL-18BP in a cell culture medium that is free of components derived from animal serum, wherein the cell culture medium comprises:
   Asparagine at a concentration ranging from about 800 to about 900 mg/L;
   Natrium Chloride at a concentration ranging from about 3000 to about 4500 mg/L;
   Selenite at a concentration ranging from about 0.005 to about 0.015 mg/L;
   Wheat hydrolysate at a concentration ranging from about 5000 to about 15000 mg/L; and
   Insulin at a concentration ranging from about 2.5 to about 6 mg/L.

2. The process according to claim 1, further comprising the step of collecting the medium.

3. The process according to claim 2, further comprising isolating the IL-18BP.

4. The process according to claim 3, further comprising formulating the isolated protein with a pharmaceutically acceptable carrier to obtain a pharmaceutical composition.

5. The process according to claim 1, wherein the cells are Chinese Hamster Ovary (CHO) cells.

6. The process according to claim 1, wherein the medium further comprises glucose at a concentration ranging from about 500 to about 5500 mg/L.

7. The process according to claim 1, wherein the medium further comprises amino acids selected from Alanine, Arginine, Aspartic Acid, Cysteine, Glutamic Acid, Glycine, Histidine, Isoleucine, Leucine, Lysine, Methionine, Phenylalanine, Proline, Serine, Tryptophan, Tyrosine, Threonine, and Valine, but no Glutamine.

8. The process according to claim 1, wherein the medium further comprises Alanine, Arginine, Aspartic Acid, Cysteine, Glutamic Acid, Glycine, Histidine, Isoleucine, Leucine, Lysine, Methionine, Phenylalanine, Proline, Serine, Tryptophan, Tyrosine, Threonine, Valine and Glutamine.

9. The process according to claim 1, wherein the medium further comprises vitamins selected from Biotin, Pantothenate, Choline chloride, Folic Acid, Myo-Inositol, Niacinamide, Pyridoxine, Riboflavin, Vitamin B12, Thiamine, and Putrescine.

10. The process according to claim 1, wherein the medium further comprises salts selected from $CaCl_2$, KCl, $MgCl_2$, Sodium Phosphate, $CuCl_2$, and $ZnCl_2$.

11. The process according to claim 1, wherein the medium further comprises a buffer.

12. The process according to claim 1, further comprising fatty acids selected from Arachidonic Acid, Linoleic Acid, Oleic Acid, Lauric Acid, or Myristic Acid.

13. The process according to claim 1, wherein the medium further comprises Cyclodextrin.

14. The process according to claim 1, wherein the medium further comprises a soy hydrolysate.

15. The process according to claim 1, wherein the medium further comprises hydrocortisone.

16. The process according to claim 1, wherein the medium further comprises a protective agent and wherein said protective agent is poloxamer 188.

17. The process according to claim 1, wherein the medium further comprises pyruvate.

* * * * *

UNITED STATES PATENT AND TRADEMARK OFFICE
CERTIFICATE OF CORRECTION

PATENT NO. : 7,553,665 B2  
APPLICATION NO. : 10/590212  
DATED : June 30, 2009  
INVENTOR(S) : Yehoshua Aloni, Orit Aharonovitz and Thierry Ziegler Page 1 of 1

It is certified that error appears in the above-identified patent and that said Letters Patent is hereby corrected as shown below:

Column 5,  
Line 11, "relates to the use cell" should read --relates to the use of a cell--.

Column 6,  
Line 18, "970, 675, 980" should read --970, 975, 980--.

Column 12,  
Line 54, "WO02096466" should read --WO02096456--.

Signed and Sealed this

First Day of September, 2009

David J. Kappos  
*Director of the United States Patent and Trademark Office*